United States Patent [19]

Elford et al.

[11] Patent Number: 5,366,996
[45] Date of Patent: Nov. 22, 1994

[54] METHOD OF TREATING HEMOGLOBINOPATHIES

[76] Inventors: Howard L. Elford, 3313 Gloucester Rd., Richmond, Va. 23227; Bartholomeus van't Riet, 3419 Noble Ave., Richmond, Va. 23222

[21] Appl. No.: 986,861

[22] Filed: Dec. 7, 1992

[51] Int. Cl.$^5$ ............................................. A61K 31/19
[52] U.S. Cl. ....................................................... 514/575
[58] Field of Search ........................................... 514/575

[56] References Cited

U.S. PATENT DOCUMENTS 4,263,322  4/1981  van't Riet et al. ................... 424/324
4,448,730  5/1984  van't Riet et al. ............ 260/500.5 H

OTHER PUBLICATIONS

Letvin et al New Eng. J. Med. 310, 869 (1984).
Goldberg et al. id. 323, 366 (1990).
Charache et al, Blood 69 109 (1987).
Vieth et al, New Eng. J. Med. 313, 1571 (1985).
Constantoulakis et al, Blood 77, 1326 (1991).
Merck Manual (15th ed.): Anemias p. 277, 1987.
(Abstract) Pace et al, Blood 78 S1 203a (1991).
Dover & Charache, Annal N.Y. Academy of Science 565, 222 (1989).

*Primary Examiner*—Marianne M. Cintins
*Assistant Examiner*—M. Moezie
*Attorney, Agent, or Firm*—James L. Rowe

[57] ABSTRACT

A therapeutic process for treating anemias in primates, including man, particularly those anemias of genetic origin including sickle-cell anemia, which comprises administering to an anemic primate an amount of a polyhydroxy benzoic, mandelic or phenylacetic acid derivative as specified at a dose level sufficient to increase fetal hemoglobin.

10 Claims, No Drawings

METHOD OF TREATING HEMOGLOBINOPATHIES

BACKGROUND OF THE INVENTION

This invention relates to a method of treating hemoglobinopathies utilizing polyhydroxybenzoic acid derivatives, such as polyhydroxybenz-amides, -hydroxamic acids, -amidoximes, -amidines, -amidates, -esters, as well as the corresponding polyhydroxyphenylacetic acid and polyhydroxymandelic acid derivatives, and compounds of related structure as the active pharmacologic agents.

Hemoglobinopathies encompass a number of anemias of genetic origin in which there is decreased production and/or increased destruction (hemolysis) of red blood cells (RBCs). The blood of normal adult humans contains hemoglobin (designated as HbA) which contains two pairs of polypeptide chains designated alpha and beta. Fetal hemoglobin (HbF), which produces normal RBCs, is present at birth, but the proportion of HbF decreases during the first months of life and the blood of a normal adult contains only about 2% HbF. There are genetic defects which result in the production by the body of abnormal hemoglobins with a concomitant impaired ability to maintain oxygen concentration. Among these genetically derived anemias are included thalassemia, Cooley's Disease and, most importantly, sickle-cell anemia (HbS disease).

Sickle-cell anemia is an inherited chronic hemolytic anemia characterized by sickle-shaped RBCs present in part of the offspring of parents who are both heterozygotes to the abnormal gene which causes the sickling disease. This disease is recessive, and heterozygotes carrying this gene show no blatant anemia or similar abnormality. Thus, only about 25% of the children of parents who are both heterozygous are expected to be homozygotic to this abnormal gene and will develop sickle cell anemia and eventually sickling crisis (aplastic crisis). Few homozygotes live past 40 years of age and may show abnormal body growth patterns. The gene which characterizes sickling trait causes valine to be substituted for glutamic acid in the sixth peptide of the beta chain, thus producing HbS rather than HbA. Deoxygenated HbS is much less soluble than deoxy HbA and it forms a semisolid gel of rodlike tactoids, thus causing the RBCs produced from HbS to assume a sickle shape. These abnormallyshaped RBCs form a sort of sludge. In addition, these HbS RBCs are more fragile than normal RBCs and hemolyze more easily, thus leading eventually to anemia.

The clinical manifestations of an aplastic crisis in sickle-cell homozygotes include arthralgia with fever, jaundice, aseptic necrosis of the femoral head, chronic punched-out ulcers about the ankles plus episodes of severe abdominal pain with vomiting. Thrombosis and/or infarction may also be present. Laboratory findings include a monocytic anemia with an RBC count in the range $2-3 \times 10^6$.

Early death, usually before 40, is caused by intercurrent infections (especially tuberculosis), multiple pulmonary emboli or thrombosis of a vessel supplying a vital area.

In the past, treatment of sickle-cell anemia was symptomatic only. Recently, however, it has been found that drugs which can increase production of the normal fetal hemoglobin HbF (since clearly, drugs cannot alter the HbS/HbA ratio in homozygotes since it is genetically determined), can tide a homozygote over the aplastic crisis, and thus potentially prolong their life. It has been known for some time that drugs such as 5-azacytidine, cytarabine and hydroxyurea could augment HbF production in anemic monkeys—see Levine et al, New Eng. J. Med. 310:869 (1984) and references cited therein. Recent limited clinical studies have shown that these drugs do indeed increase HbF production in patients with sickle-cell disease—see Goldberg et al, New Eng. J. Med. 323:366 (1990) for hydroxyurea; Charache, Dover and co-workers, Blood 69:109 (1988); 6th Annual Conf. on Hemoglobin Switching, Sep. 2, 1988 for 5-azacytidine and hydroxyurea; Veith et al, New Eng. J. Med. 313:1571 (1985) for cytarabine and hydroxyurea.

In addition to the previously cited experiments in anemic monkeys (Levin et al loc. cit.), more recently Constantoulakis et al, Blood 77:1326 (1991) have developed a new model system for studying the induction of fetal hemoglobin (HbF) by various drugs, using adult transgenic mice carrying the human A(gamma) globin gene linked to the locus control region regulatory sequences and expressing heterocellularly HbF. Erythropoietin, 5-azacytidine, hydroxyurea and butyric acid esters (butyrate), all known in vivo HbF inducers in adult humans, also induced HbF in this model.

SUMMARY OF THE INVENTION

This invention provides a method of treating hemoglobinopathies of genetic origin by increasing the production of fetal hemoglobin in a human suffering from one of said hemoglobinopathies by administering to said human a dose of a compound according to the following formula effective to produce an increase in fetal hemoglobin:

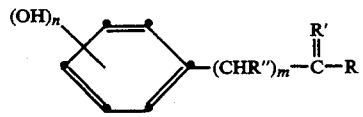

wherein n is 2-5, m is 0 to 1, R is NHOH, NH$_2$, NHR''', N(R''')$_2$, OH, O-C$_{1-3}$alkyl or O-phenyl, R' is O, NH or NOH, R'' is H or OH, and R''' is C$_1$-C$_6$ alkyl. Also included within the scope of the above formula are the pharmaceutically-acceptable salts of compounds depicted thereby where chemically feasible, as well as the phenolic acetyl or similar phenolic esters of compounds according to the above formula which, by their ready hydrolysis to the free hydroxyl derivative, act as prodrugs. Compounds according to above formula in which R=OH and R'=O(carboxylic acids) are of particular interest. The free acids, though less active when administered directly than the derivatives with R=other than OH (e.g. amides and esters) may be converted in the mammalian body to the carboxylic acid which may be, in fact, the active principle in treating anemias and/or increasing fetal hemoglobin.

Compounds illustrative of the above formula include:

2,3,4-trihydroxyphenylacetamidine
3,4,5-trihydroxyphenylacetamidine
2,4,5-trihydroxyphenylacetamidine
2,3,5-trihydroxyphenylacetamidine
3,4-dihydroxyphenylacetohydroxyamidoxime
3,5-dihydroxyphenylacetohydroxyamidoxime 2,3-dihydroxyphenylacetohydroxyamidoxime
2,3,4-trihydroxyphenylacetohydroxyamidoxime
2,3,5-trihydroxyphenylacetohydroxyamidoxime
2,4,5-trihydroxyphenylacetohydroxyamidoxime
3,4,5-trihydroxyphenylacetohydroxyamidoxime,
3,4-dihydroxyphenylacetamidoxime
3,5-dihydroxyphenylacetamidoxime
2,3-dihydroxyphenylacetamidoxime
2,5-dihydroxyphenylacetamidoxime
2,4-dihydroxyphenylacetamidoxime
2,3,4-trihydroxyphenylacetamidoxime
3,4,5-trihydroxyphenylacetamidoxime
2,4,5-trihydroxyphenylacetamidoxime
2,3,5-trihydroxyphenylacetamidoxime
ethyl 3,4-dihydroxyphenylacetamidate
methyl 2,3-dihydroxyphenylacetamidate
n-propyl 3,5-dihydroxyphenylacetamidate
isopropyl 2,3,4-trihydroxyphenylacetamidate
methyl 3,4,5-trihydroxyphenylacetamidate
methyl 2,4,5-trihydroxyphenylacetamidate
methyl 2,3,4,5-tetrahydroxyphenylacetamidate
ethyl 2,3,4,6-tetrahydroxyphenylacetamidate
methyl 2,3,4,5,6-pentahydroxyphenylacetamidate
2,3,4,5-tetrahydroxyphenylacetamidine
2,3,4,6-tetrahydroxybenzylacetamidine
2,3,5,6-tetrahydroxyphenylacetamidine
2,3,4,5,6-pentahydroxyphenylacetamidine
2,3,4,5,6-pentahydroxyphenylacetohydroxyamidoxime
2,3,5,6-tetrahydroxyphenylacetohydroxyamidoxime
2,3,4,5-tetrahydroxyphenylacetohydroxyamidoxime
ethyl 2,3,5-trihydroxyphenylacetamidate
2,3-dihydroxyphenylacetamidine
3,4-dihydroxyphenylacetamidine
3,5-dihydroxyphenylacetamidine
2,4-dihydroxyphenylacetamidine
2,5-dihydroxyphenylacetamidine
2,3-dihydroxybenzohydroxyamidoxime
3,4-dihydroxybenzohydroxyamidoxime
methyl 2,3,4-trihydroxybenzamidate
isopropyl 3,5-dihydroxybenzamidate
ethyl 3,4,5-trihydroxybenzamidate
ethyl 3,4-dihydroxybenzamidate
3,4-dihydroxybenzamidoxime
3,4,5-trihydroxybenzamidoxime
2,3,5-trihydroxybenzamidoxime
n-propyl 2,4,5-trihydroxybenzamidate
2,3-dihydroxybenzamidoxime
ethyl 2,4-dihydroxybenzamidate
ethyl 3,4,5-trihydroxybenzamidate
2,5-dihydroxybenzohydroxyamidoxime
3,4,5-trihydroxybenzamidine
2,3-dihydroxybenzamidine
2,3,4-trihydroxybenzamidine
3,4-dihydroxybenzamidine
dl-2,4,5-trihydroxymandelamidine
2,4,5-trihydroxybenzamidine
3,5-dihydroxybenzamidine
dl-3,4-dihydroxymandelamidine
dl-3,4,5-trihydroxymandelamidine
dl-2,3-dihydroxymandelamidine
dl-2,3,4-trihydroxymandelohydroxyamidoxime
dl-2,4,5-trihydroxymandelohydroxyamidoxine
2,3,4-trihydroxybenzamidoxime
2,3,4-trihydroxybenzohydroxyamidoxime
3,4,5-trihydroxybenzohydroxyamidoxime
ethyl 2,3-dihydroxybenzamidate
dl-3,4-dihydroxymandelamidoxime
dl-3,4,5-trihydroxymandelohydroxyamidoxime
dl-3,5-dihydroxymandelohydroxyamidoxime
dl-3,4-dihydroxymandelohydroxyamidoxime
dl-2,4-dihydroxymandelamidoxime
dl-2,3-dihydroxymandelamidoxime
dl-3,5-dihydroxymandelamidoxime
dl-2,3,4-trihydroxymandelamidoxime
dl-3,4,5-trihydroxymandelamidoxime
dl-2,4,5-trihydroxymandelamidoxime
dl-methyl 3,4-dihydroxymandelamidate
dl-ethyl 3,5-dihydroxymandelamidate
dl-n-propyl 2,3-dihydroxymandelamidate
dl-methyl 2,3,4-trihydroxymandelamidate
dl-ethyl 3,4,5-trihydroxymandelamidate
dl-ethyl 2,3,5-trihydroxymandelamidate
dl-isopropyl 2,4,5-trihydroxymandelamidate
2,4,6-trihydroxybenzohydroxamic acid
2,4-dihydroxybenzohydroxamic acid
2,5-dihydroxybenzohydroxamic acid
2,3,4-trihydroxybenzohydroxamic acid
3,4,5-trihydroxybenzohydroxamic acid
2,3,5-trihydroxybenzohydroxamic acid
2,4,5-tridydroxybenzohydroxamic acid
2,3,6-trihydroxybenzohydroxamic acid
2,3-dihydroxybenzohydroxamic acid
3,4-dihydroxybenzohydroxamic acid
N-ethyl 3,4,5-trihydroxybenzamide
3,4-dihydroxyphenylacetic acid
3,4,5-trihydroxyphenylacetic acid
phenyl 2,3,4-trihydroxybenzoate
3,4-dihydroxyphenylacetohydroxamic acid
N-dimethyl-3,4-dihydroxyphenylacetamide
2,3-dihydroxymandelohydroxamic acid
2,3,4,5-tetrahydroxybenzamide
ethyl 3,4-dihydroxyphenylacetate
n-propyl 3,4-dihydroxymandelate
3,4,5-triacetoxybenzamide
3,4,5-tripivaloxybenzamide and like compounds. The compounds of this invention are prepared by the procedures set forth in U.S. Pat. Nos. 4,263,322, 4,394,389, 4,623,659, 2,849,480, 3,639,443, 4,448,730, 4,623,659, and references cited therein.

It will be apparent to those skilled in the art that other phenolic blocking groups, in addition to the acetyl and pivalo group specified above, may be employed to provide pro-drugs, including other lower alkanoic esters, phenacyl esters and the like, the only requirement being that the mammalian organism is easily able to convert the pro-drug to the active drug.

An effective dose level of a compound according to the above formula for the treatment of hemoglobinopathies including sickle-cell anemia, Cooley's anemia, thalassemia, hemoglobin C disease and hemoglobin S-C disease by increasing the production of fetal hemoglobin is in the range 0.1 g to 7 g per meter$^2$ of body surface. A compound particularly useful in the therapeutic processes of this invention is 3,4-dihydroxybenzohydroxamic acid (DIDOX).

When tested in the transgenic mouse model described above, administration of DIDOX increased F (fetal) reticulocytes, F cells and gamma-RNA synthesis. The following protocol was used: dose=400 mg/kg mouse body weight for 5 days, off 2 days, cycle repeated several times, drug administered iv as an isotonic solution. In normal baboons (not anemic), DIDOX increased F cells, F reticulocytes and gamma RNA. Another drug coming within the scope of the above formula which gave excellent activity in preliminary tests was gallamidoxime (TRIMIDOX).

It will be apparent that the drugs of this invention, by their ability to increase HbF in HbS homozygotes cannot only ameliorate but even abort sickling crises. In addition, there is the possibility that the drug administered routinely before HbF has decreased in newborns could prevent the poor physical development often seen in part if not in whole.

BIOLOGICAL TESTING

Mononuclear Cell Culture Induction Assay

Mononuclear cells were isolated from adult heparinized peripheral blood after layering on a cushion of Ficoll-sodium Metrizoate. Nonadherent cells were grown for 14 days in methylcellulose culture in the presence of varying concentrations of 3,4-dihydroxybenzohydroxamic acid (Didox). Circulating erythroid progenitors (BFU-E$_s$) colonies were enumerated and labeled with tritiated leucine. Relative globin chain biosynthesis ratios were determined by densitometric scanning of autoradiograms from isoelectric focusing gels. The $\gamma/\gamma+\beta$ ratio is an indicator of HbF.

As illustrated in the table below, the inclusion of Didox in

| Treatment of Culture | Conc. (M) | No. of BFU-E Colonies* | $\gamma/\gamma + \beta$ Ratio Mean Corrected |
|---|---|---|---|
| None | 0 | 43 | 0.0035 |
| Didox | $10^{-6}$ | 32 | 0.0055 |
| Didox | $5 \times 10^{-6}$ | 31 | 0.0015 |
| Didox | $10^{-5}$ | 37 | 0.0155 |
| Didox | $5 \times 10^{-5}$ | 19 | 0.0815 |

*per $10^5$ cells plated the growth media at $10^{-5}$M caused a five-fold increment in HbF as indicated by the increased $\gamma/\gamma+\beta$ ratio without a significant effect on the number of BFU-E colonies. Didox at a concentration $5\times10^{-5}$M increased the $\gamma/\gamma+\beta$ ratio (HbF) 20 fold with only an approximate 50% inhibition of BFU-E colony formation.

Transgenic Mouse Model

Transgenic mice carrying the human fetal ($\gamma$) globin genes were developed to study developmental control of human globin genes. This is possible since in contrast to humans who have three stages of Hb development, embryonic, fetal and adult, mice have only two stages of Hb development, embryonic and adult. Therefore, the production of HbF is the consequence of the expression of the human fetal globin gene in the transgenic mouse. The results reported below employed transgenic mice containing human gamma-globin gene constructs $\mu$LCR-$^A\gamma$ and $5^1$ HS III-$^A\gamma$(LCR=locus control region and HS=hypersensitive site). This model and the effect of known drugs that induce HbF in the model are described in Constantoulakis et al, Blood, 77, 1326, (1991). The determination of hematologic parameters HbF, reticulocytes (RET), and globin chain analysis ($\gamma/\gamma+\beta$) was carried out as described in the Blood reference noted above ($\beta\beta$). A transgenic mouse carrying the human $\gamma$ globin construct $\mu$LCR-$^A\beta$ treated with hydroxyurea (HU) at 400 mg/kg/d for 5 days with a 2 day rest between treatment cycles caused an increase in F cells from a base line of 31.2% to a peak of 58.5% in the fifth cycle week. The F RET increased from a base line of 38.1% to 66.3%. During the HU treatment period, the % RET increased from a base line value of 5% to 22%. The measurement of fetal globin chain biosynthesis, the $\gamma/\gamma+\beta$ ratio, had a base line value of approximately 0.0025 which increased to a peak value of 0.043 on day 20. When a transgenic mouse carrying the same human $\gamma$ globin gene construct $\mu$LCR-$^A\gamma$ was treated with Didox consisting of daily i.p. injection of 100 mg/kg/d for 5 days each week for a total of 5 weeks, the base line value of F RET cells increased from 41.6% to 74.7% at the end of a 5 week cycle. Also the F cells increased from a base line value of 40.3% to 68.6%. In contrast to the HU treated transgenic mouse, the % RET was not appreciably altered at a dose of 100 mg/kg and still produced an appreciable enhancement of F RET and F cells as well as $\gamma$ globin synthesis as noted in the following. In the Didox treated transgenic mouse at 100 mg/kg/d the base line value ratio was 0.004 and increased to 0.044 at the end of treatment. In a transgenic mouse treated with Didox on the same schedule as above but a dose of 450 mg/kg, similar increases in F RET and F cells occurred, however, there was a more pronounced effect on the $\gamma/\gamma+\beta$ ratio. The base line value was 0.014 and increased to 0.086 with the Didox treatment. At this dose Didox did cause a 3 fold increase in % RET.

Treatment of a $5^1$ HS III-A$\gamma$ transgenic mouse with Didox at 450 mg/kg/d on the same daily $\times$5 per week schedule as used above produced a greater than 10 fold (1.28% to 14.35%) increase in F RET and an increase of greater than 4 fold in F cells (2.86% to 11.0%) and a greater than 10 fold increase in the $\gamma/\gamma+\beta$ ratio over observed base line values. However, there was evidence of myelosuppression by a marked increase in % reticulocytes during the third week of Didox treatment.

Anemic Baboon Model

A single baboon was made and kept anemic by removal of up to 15% of its blood volume on a near-daily basis to maintain a hematocrit of 20 to 25%. Hematologic studies included measurements of Hb, hematocrit (HCT), white blood cells, (WBC), and reticulocytes (RET). Determination of F cells and F RET was performed in a similar way as previously described in Blood, 63, 201, (1984).

The 26 day phlebotomy prior to drug treatment interval caused a reduction in Hb and HCT and an increase in % RET, F RET, and F cell. The decrease in Hb and HCT were 38% and 35% respectively. There was a corresponding increase of 7.1, 1.7, and 2.6 fold in RET, F RET, and F cell respectively. Treatment of the anemic baboon on a cycle of daily i.p. injections of Didox for 5 days followed by two days without drug at a does of 250 mg/kg/ for four 5-day treatment cycles and then one cycle of daily $\times$5 treatments with a prior two-day rest at a dose of 300 mg/kg only produced a modest 25% maximum reduction of Hb and HCT during this treatment period over the anemia induction by phlebotomy alone. On the other hand, the treatment protocol with Didox caused a 5.1 fold further increase in F RET and a 2.5 fold further enhancement of F cells beyond the effect of phlebotomy alone. These values are 8.8 and 6.5 fold higher than the base line values of the baboon. These results on the induction of F cell and F RET by Didox are equal or superior to other cytoreductive agents with less myelosuppression.

We claim:

1. A method for treating anemias in primates which comprises administering to an anemic primate in need of treatment for said anemia a dose of a compound of the formula

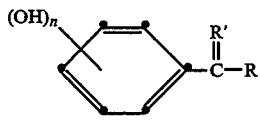

wherein n is 2–5, R is NHOH, R' is O, or pharmaceutically-acceptable salts thereof and readily hydrolyzable phenolic esters thereof effective to treat said anemia.

2. A method according to claim 1 in which a human is the primate being treated.

3. A method according to claim 1 in which the anemia is caused by a hemoglobinopathy.

4. A method according to claim 3 in which the hemoglobinopathy is sickle-cell anemia.

5. A method according to claim 1 in which the compound employed is 3,4-dihydroxybenzohydroxamic acid.

6. A method according to claim 1 in which the dose administered is in the range of 0.1 to 7 g per meter$^2$ of body surface.

7. A therapeutic process for increasing the fetal hemoglobin in a human suffering from a hemoglobinopathy of genetic origin which comprises administering to said human an amount of a compound effective to increase fetal hemoglobin, said compound having the formula

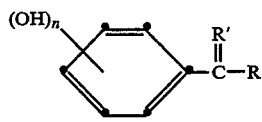

wherein n is 2–5, R is NHOH, R' is O, or pharmaceutically-acceptable salts thereof and readily hydrolyzable phenolic esters thereof effective to treat said anemia.

8. A process according to claim 7 in which the human is suffering from sickle cell anemia.

9. A process according to claim 7 in which the compound administered is 3,4-dihydroxybenzohydroxamic acid.

10. A process according to claim 7 in which the dose of the compound is in the range of 0.1 g to 7 g per meter$^2$ of body surface.

* * * * *